United States Patent [19]

Teubner et al.

[11] Patent Number: 5,219,351
[45] Date of Patent: Jun. 15, 1993

[54] MAMMOGRAPH PROVIDED WITH AN IMPROVED NEEDLE CARRIER

[75] Inventors: Joachim Teubner, Schwetzingen, Fed. Rep. of Germany; Jean-Yves DiBartolomeo, Paris; Didier Rouchy, Les Clayes Sous Bois, both of France

[73] Assignee: General Electric CGR S.A., France

[21] Appl. No.: 780,789

[22] Filed: Oct. 23, 1991

[30] Foreign Application Priority Data

Oct. 24, 1990 [FR] France .................. 90 13180

[51] Int. Cl.⁵ .......................................... A61B 19/00
[52] U.S. Cl. .................................................. 606/130
[58] Field of Search ................ 128/653.1; 606/130; 378/37

[56] References Cited

U.S. PATENT DOCUMENTS

| | | | |
|---|---|---|---|
| 4,230,117 | 10/1980 | Anichkov | 606/130 |
| 4,386,602 | 6/1983 | Sheldon et al. | 606/130 |
| 4,875,478 | 10/1989 | Chen | 378/37 |
| 5,018,176 | 5/1991 | Romeas et al. | 378/37 |
| 5,056,523 | 10/1991 | Hotchkiss, Jr. et al. | 378/37 |
| 5,078,142 | 1/1992 | Siczek et al. | 378/37 |
| 5,163,430 | 11/1992 | Carol | 606/130 |

FOREIGN PATENT DOCUMENTS

| | | |
|---|---|---|
| 0146511 | 6/1985 | European Pat. Off. . |
| 0288187 | 10/1988 | European Pat. Off. . |
| 0957888 | 9/1982 | U.S.S.R. .................. 606/130 |

OTHER PUBLICATIONS

Proceedings of the Institute of Mechanical Engineers, vol. 183, No. 15, 1968-69, London, Great Britain, pp. 281-292, Dawson, et al., "Bio-Engineering Approach to Sterotactic Surgery of the Brain".

Proceedings of the Annual International Conference of the IEEE Engineering in Medicine and Biology Society, vol. 11, 1989, United States, pp. 879-880, Guerrouad, et al., "S.M.O.S.: Stereotaxical Microtelmanipulator for Ocular Surgery.".

Primary Examiner—Lee S. Cohen
Assistant Examiner—Samuel Gilbert
Attorney, Agent, or Firm—Nilles & Nilles

[57] ABSTRACT

To enable a biopsy needle to be inserted into a breast under examination on a mammograph, a crank handle-shaped structure is provided which is vertically supported by a shaft and which carries a needle carrier on its handle portion, the vertical axis of rotation passing through a tumor whose position within the breast has been calculated. It is shown that the insertion distance of the needle can be predetermined and that under these conditions a variety of ways of reaching the tumor are made available by rotating the crank-handle shape about its axis. The insertion direction can be selected as a function of criteria applicable to the subsequent surgery and not solely as a function of the structure of the mammograph itself.

22 Claims, 5 Drawing Sheets

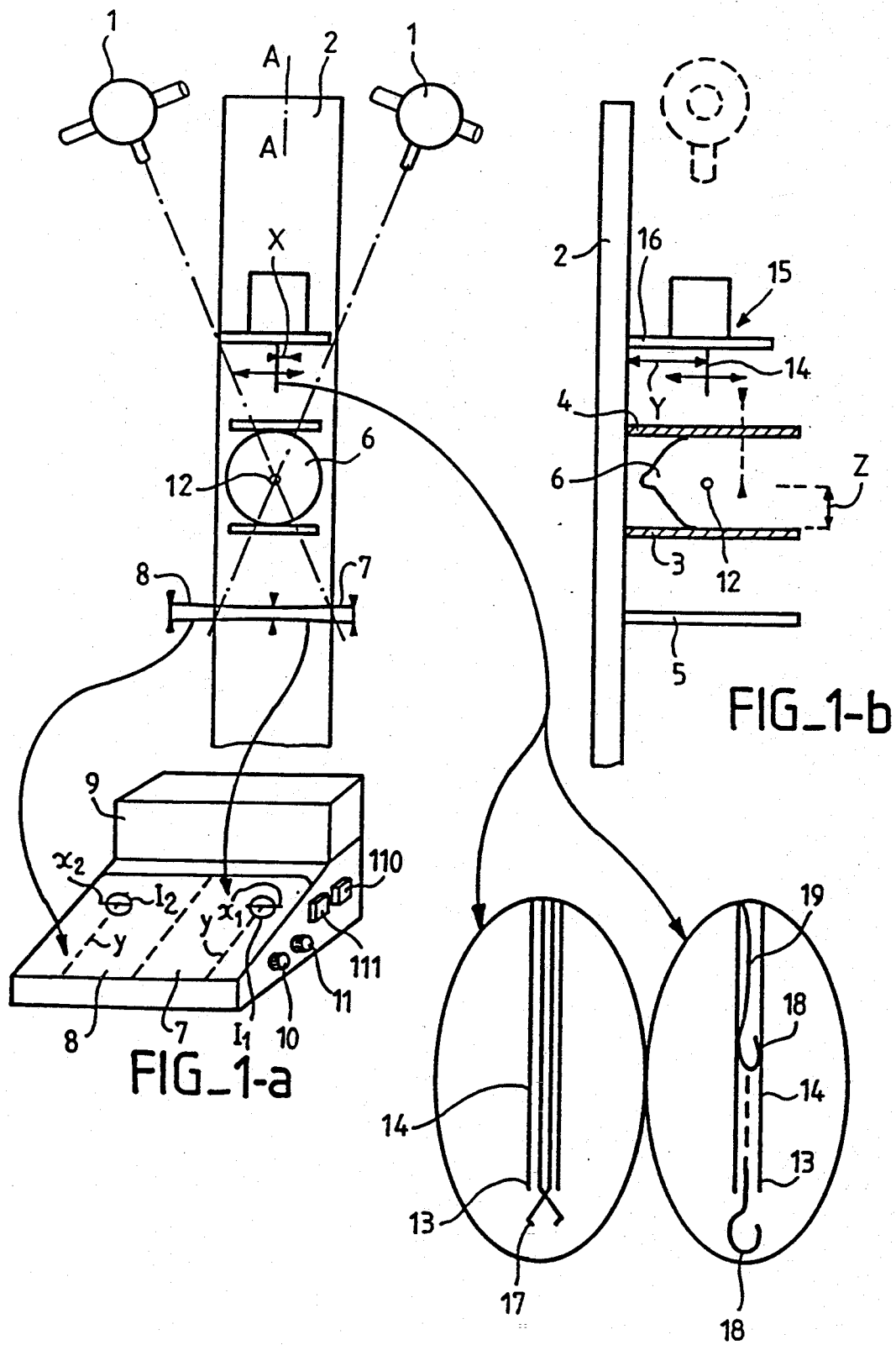

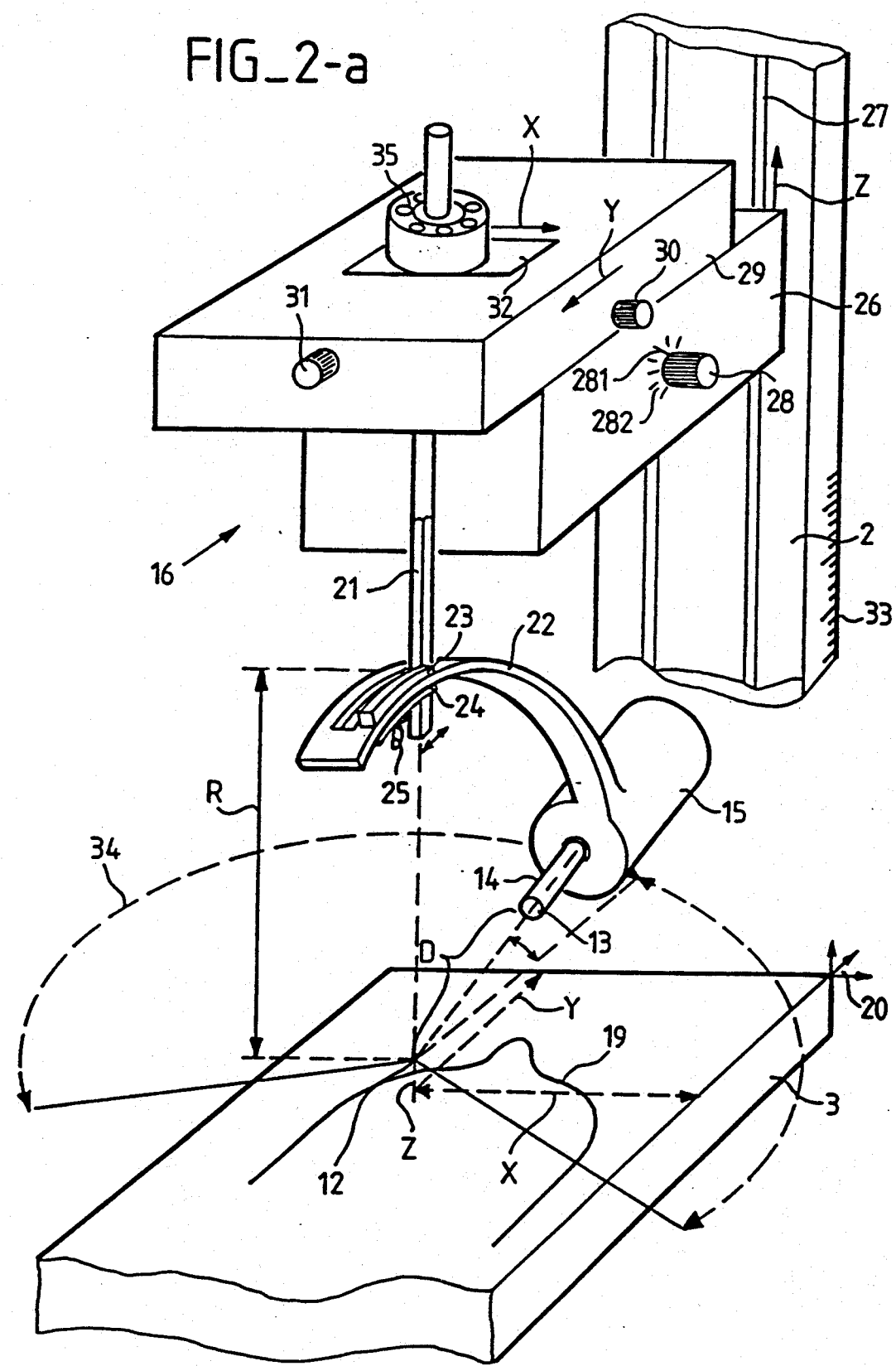

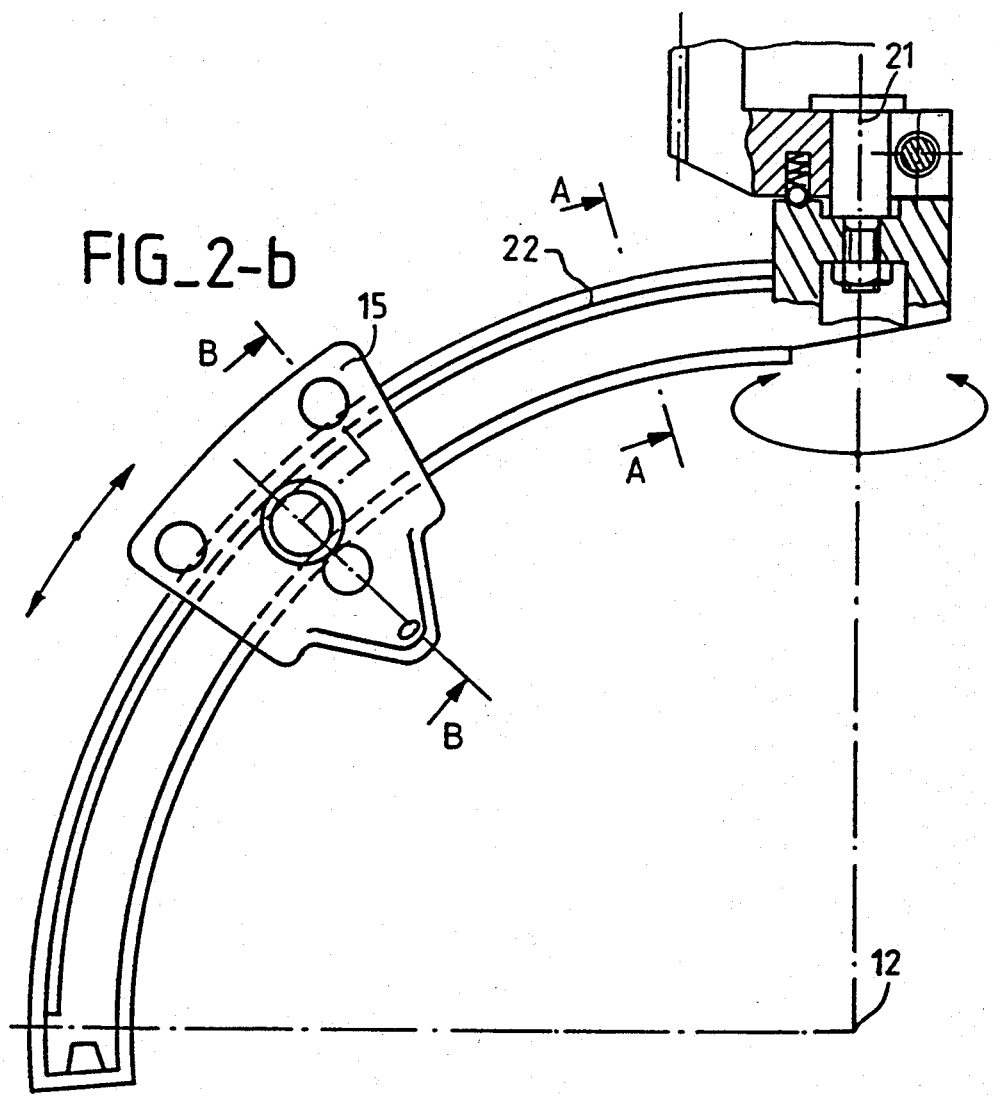
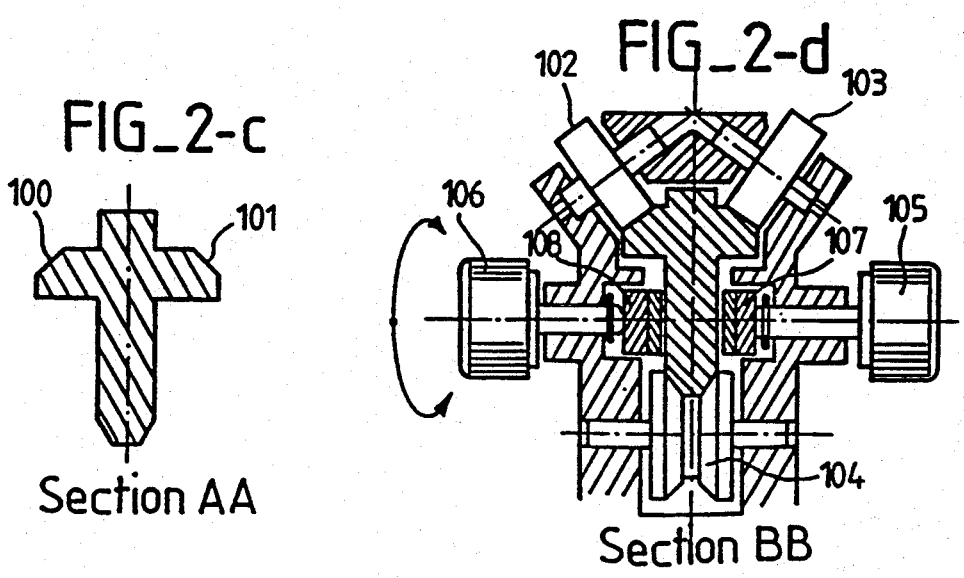

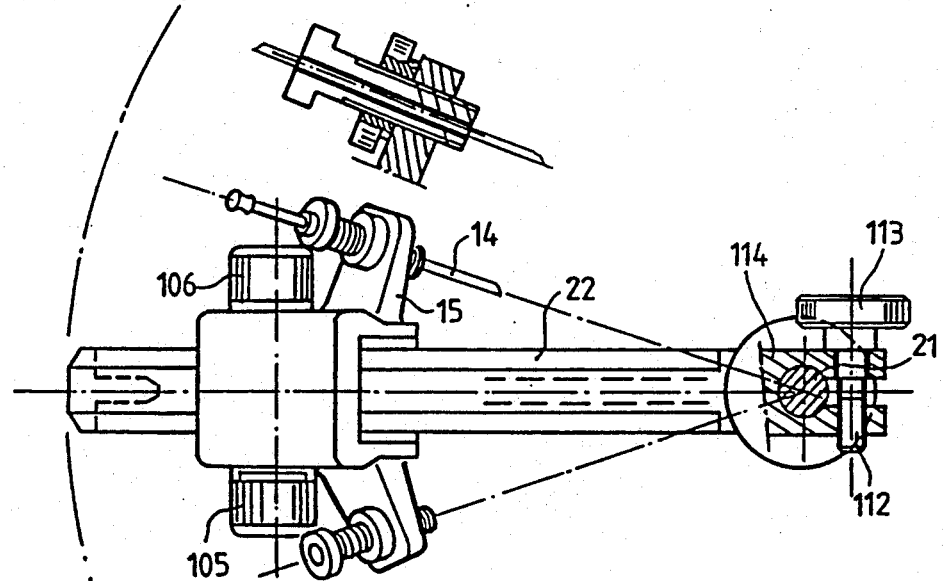
FIG_2-e
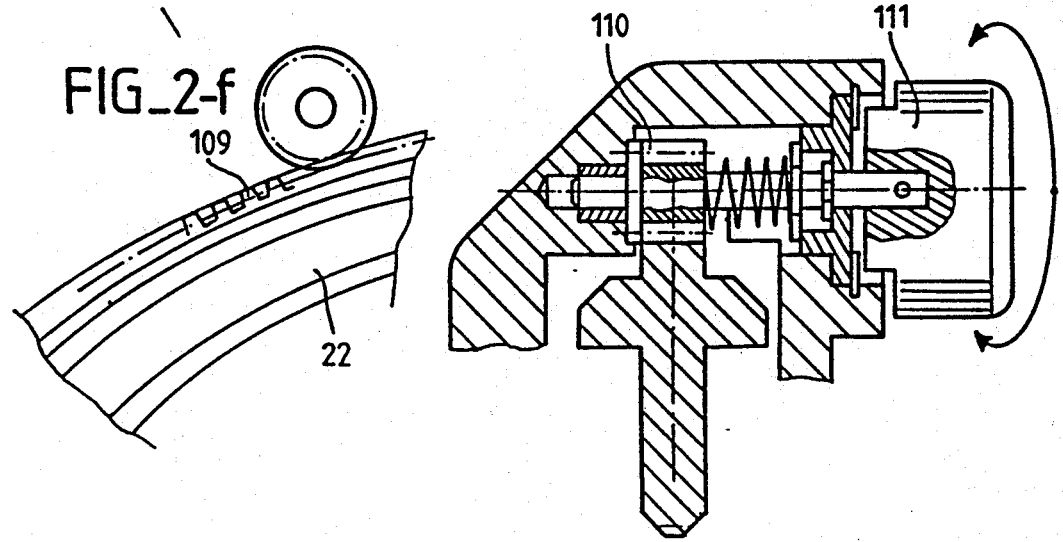
FIG_2-f
FIG_2-g

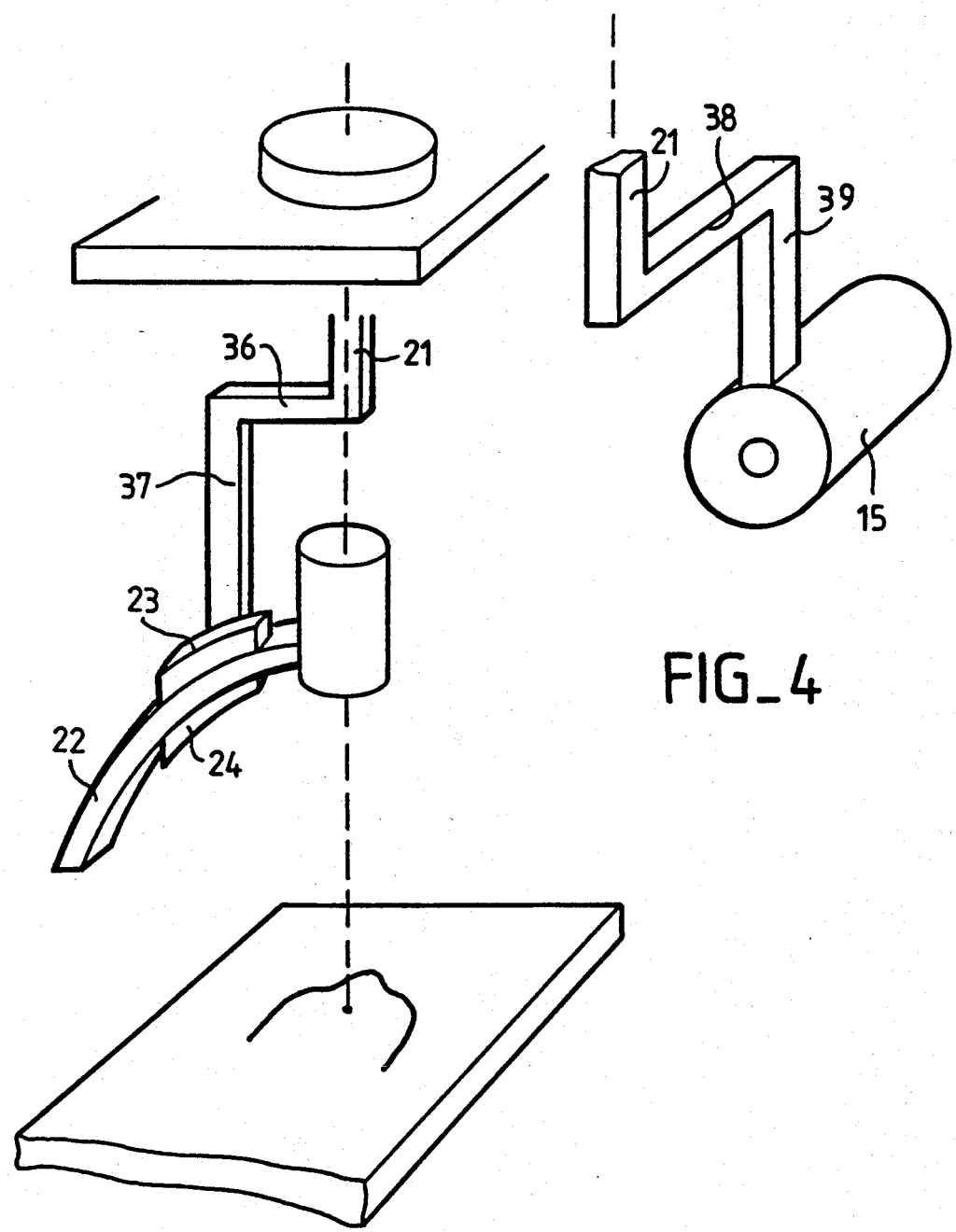
FIG_4
FIG_3

MAMMOGRAPH PROVIDED WITH AN IMPROVED NEEDLE CARRIER

The present invention relates to a mammograph provided with an improved needle carrier. It is usable more particularly in the field of medicine to prepare for taking action on the breasts of patients being examined. The invention seeks mainly to facilitate performing a biopsy or providing surgical guidance when removing a tumor.

BACKGROUND OF THE INVENTION

A mammograph normally includes a post onto which a breast-carrying plate and a moving pad are fixed. For an examination, a patient places her breast on the plate and the pad is lowered so as to compress the breast under examination and hold it in a fixed position. An X-ray tube is placed to one side of this assembly, generally above it. A cassette-carrier is placed on the opposite side and a cassette containing X-ray sensitive film is inserted therein. The X-ray tube is fixed to a bracket and the post of the bracket can tilted relative to the post of the mammograph. For stereography, an X-ray exposure is taken of the breast with the post at a given inclination on one side. The bracket carrying the X-ray tube is then tilted so that it takes up a different inclination, preferably symmetrical to the first relative to the post of the mammograph. A second X-ray exposure is then taken. After development, each of the exposures may reveal the presence of a particular disease which is to be located. In general, it is cancerous tumors that are being sought. A stereographic examination performed in this way makes it possible during subsequent stereotaxic measurement to determine the position in three dimensions of tumors detected in the breast under examination, i.e. to determine their positions relative to a three-dimensional frame of reference tied either to the cassette carrier or else to the pad, with positions being given in terms of X, Y, and Z coordinates.

FIG. 1a is a diagram of such a mammograph showing the two possible positions of the X-ray tube 1 on either side of the post 2 of the mammograph. FIG. 1b is a section on line AA in FIG. 1a. The following can be seen connected to the post 2: the breast-carrying plate 3, the moving pad 4, the cassette carrier 5, and the breast 6 under examination. During stereographic examination, two exposures 7 and 8 are taken which can be displayed on a stereotaxic apparatus 9.

The stereotaxic apparatus 9 includes cursors, and in this case there are at least two cursors $I_1$ and $I_2$ which are constituted by small circles surrounding crosses. These cursors can be displaced over the display plane of the apparatus 9 by means of measurement buttons 10 and 11. Control buttons 110 and 111 serve to select which one of the cursors $I_1$ and $I_2$ is to be moved. The buttons 10 and 11 are called "measurement" buttons because the coordinates $x_1,y$ and $x_2,y$ of the cursors are linked to the actions taken on the buttons 10 and 11. It is thus possible to place these cursors $I_1$ and $I_2$ on the image in each of the exposures 7 and 8 respectively of a tumor 12 contained in the breast. The X coordinates $x_1$ and $x_2$ and the Y coordinates y of these images can then be measured. It is then possible to deduce the X, Y, and Z coordinates of the tumor. For example:

$$Y = y$$

$$Z = ax_1 + bx_2$$

$$Z = a'x_1 + b'x_2$$

In these expressions, a, b, a', b' are axis-changing coefficients that take account of the inclination of the principal ray of the X-ray tube 1 relative to the post 2, and of the distance between the tube 1 and the film 7, 8 at the moment the exposures were taken. The way in which the X, Y, and Z positions of a tumor are calculated is known, and may be as described in French patent application No. 2 248 535 filed Oct. 17, 1974 or as described in French patent application No. 2 645 286 filed Mar. 29, 1989, for example.

Once the position of a tumor has been determined, the position of the tip 13 of a needle 14 in a needle carrier 15 is determined for the purpose of taking action. If the coordinates of the tip are $X_a$, $Y_a$, and $Z_a$, then the needle carrier 15 is displaced over a table 16 that carries it so that $X_a$ is made equal to X and $Y_a$ is made equal to Y, with $Z_a$ being sufficiently different from Z so that there is no danger of the tip 13 making contact with the breast during this displacement. The distance $Z - Z_a$ is the insertion depth, and it is determined in advance. For example, with a Stereotix apparatus made by General Electric CGR, France, this depth is 7 cm.

The needle 14 associated with a mammograph is a special needle: it is hollow. In conventional manner, two surgical tools can be inserted therein: a first tool referred to as "forceps" 17 is shown in the enlargement to the left of FIG. 1a, and another tool referred to as a "hook" 18 is shown in the enlargement to the right. The forceps is used for performing a biopsy, i.e. removing a sample of the tissue concerned. The hook is used for surgical guidance. In both cases, the manipulation is the same.

It consists in moving the needle carrier vertically along the predetermined insertion depth. The pad 4 is provided with an opening enabling the needle to be inserted. This makes it possible to keep the breast compressed during this operation. Under such conditions, the tip 13 of the needle comes to the position of the tumor 12. At this moment, or possibly previously, either the forceps 17 or the hook 18 is inserted into the needle. If a biopsy is to be performed, a sample is taken using the forceps 17, and the forceps is withdrawn from inside the hollow needle before withdrawing the hollow needle itself.

Otherwise, if it is desired to show a surgeon where action to be taken, a hook is slid down the hollow needle 14 and the hollow need is withdrawn leaving the hook to attach itself in the vicinity of the tumor. The hook 18 is attached to a thread 19 which then appears outside the breast and shows a surgeon where to go to remove the detected tumor.

As described above, the apparatus and the method of using it suffers from a drawback: when operating, the surgeon is obliged to follow the thread which terminates at the hook. The thread does not necessarily follow the best path for performing the operation. Which path is "best" may depend on the depth of tissue to be cut through or on the unattractive appearance of the post-operative scar. In addition, it can also happen that the surgeon cuts the thread and looses the marker showing the position of the hook.

According to the invention, this problem is solved by making the operation of inserting the needle completely independent from the structure of the apparatus. Thus, instead of providing a needle carrier that is displaceable in the X and the Y directions, with a needle that can be inserted along the Z direction, a needle carrier is provided that is displaceable in the X and Y directions, and optionally also the Z direction, and above all the needle is insertable in any direction. Under such circumstances, to solve automatically problems associated with locating the tumor relative to the tip of the needle, a needle carrier is provided which can be pointed towards an isocenter which is situated at the location of the tumor. The needle carrier is thus designed so that after the needle has been inserted through a predetermined length, its tip lies at the location of the tumor. Under such conditions, it becomes possible when performing a biopsy, or when installing a hook to select a route into the breast, giving rise to as little trauma as possible for the patient, and indeed which is less prone to error. For example, the more central zones of the breast may be reached from the periareolar zone. In other cases, the reference direction for installing the hook may coincide with the direction chosen by the surgeon for the incision. The thread or "clue" then serves as a much better guide for the operation. In a variant, it may be preferred for the marking hook to be tangential to the zone of pathology, thereby ensuring that it does not penetrate to the center thereof.

SUMMARY OF THE INVENTION

The present invention thus provides a mammograph comprising:

means for holding a breast of a patient between an X-ray tube and a device for taking X-ray exposures;

means for taking stereographic exposures of the breast;

biopsy or surgical guidance means for acting on the breast at a determined location;

said biopsy or surgical guidance means including a needle carrier which is displaceable relative to the breast;

said needle carrier including a needle whose tip is displaceable along a selected length between a retracted position and an inserted position; and a stereotaxic assembly associated with the above three means to calculate the position of the location at which action is to be taken;

wherein the mammograph includes:

pointing means to enable the biopsy needle carrier to be pointable towards an isocenter situated at the determined location;

said pointing means including a circular arc itself carried by a rotary shaft to provide two degrees of freedom in pointing the needle.

BRIEF DESCRIPTION OF THE DRAWINGS

Embodiments of the invention are described by way of example with reference to the accompanying drawings, in which:

FIGS. 1a and 1b are described above and show the essential components of a mammograph usable in the prior art and also in the invention;

FIGS. 2a to 2g are simplified views of a device of the invention enabling isocentric pointing of a needle, the views being respectively a perspective view, a side view, two sections, a plan view, another side view, and another section through a preferred embodiment of the pointing means;

FIG. 3 shows an improvement of the device shown in FIGS. 2a to 2g; and

FIG. 4 shows a simplified embodiment of the invention.

DETAILED DESCRIPTION

FIG. 2a is a diagram of a needle carrier of the invention showing the mechanical architecture that leads to isocentric pointing. Above the breast-carrying plate 3 there can be seen an outline 19 representing the presence of a breast, and more specifically the location 12 as calculated using the stereotaxic device 9 and where it is suspected that a tumor is present. The location 12 is defined by X, Y, and Z coordinates tied to a frame of reference 20 integral with the plate 3. It would naturally be possible to select any other frame of reference, possibly integral with some other part of the apparatus, with the appropriate axis changes then being performed. The needle carrier 15 has the special feature of pointing permanently at the tumor 12. To this end, it is fixed on a rotary shaft 21 whose axis passes through the tumor 12. In one example, the needle carrier 15 is fixed to the shaft 21 by a circular arc 22 enabling the needle carrier 15 to take up any elevation angle lying in the range vertical (FIG. 3) to an upwardly tilted angle that is at least a little below the horizontal. It can naturally occupy any intermediate position between these two extremes. To change position, the arc 22 may slide between two skids 23 and 24 (FIG. 2a) which are secured to the shaft 21. For example, at least one of them is welded thereto. A control handle 25 serves to move the skids towards each other and thus lock the arc 22 against sliding. The needle carrier is then held at a given angle of elevation.

FIGS. 2b to 2g nevertheless show a preferred different solution in which the arc 22 is fixed with the needle carrier 15 sliding along the arc. The arc 22 has a T-shaped section with two flanges provided at their top ends with chamfers 100 and 101. Wheels 102 and 103 (FIG. 2d) are mounted free to rotate relative to the needle carrier 15 and bear against these chamfered ends Another wheel 104 of the needle carrier 15 is shaped like a pulley wheel with a peripheral groove that exerts reaction on the base of the T-shape of the arc. The base is likewise chamfered. For adjustment purposes on assembly, the axle of the wheel 104 is eccentric. By adjusting the position of an eccentric, the extent to which the needle carrier carriage clamps the arc can be adjusted.

To hold the carriage on the arc 22, the carriage which extends generally around the arc is provided with two screw knobs 105 and 106 enabling break pads 107 and 108 to be pressed against the flanks of the arc. The knobs are screwed into the carriage. FIGS. 2f and 2g also show that the top of the T-shape of the arc 22 is provided with a rack 109. A pinion 110 driven by a knob 111 likewise supported by the needle carrier 15, meshes with the rack and enables the needle carrier to be displaced. This displacement may be motor-driven. A clamping screw 112 (FIG. 2e) driven by a knob 113 serves to clamp a collar 114 on the arc 22 about the circular shaft 21. Any desired azimuth position can thus be taken up.

The table 16 (FIG. 2a) carrying the needle carrier 15 via the shaft 21 is preferably displaceable along three directions, x, y, and z. For example, it comprises firstly a support 26 slidable in slideways 27 on the post 2 of the mammograph under the control of an adjustment button 28 having a cursor mark 281 which moves over graduations 282. In practice, the button 28, the mark 281 and the graduations 282 may be replaced by motor-driven means controlled by a micro processor capable of interpreting the height z as a height that depends on the height Z of the tumor. It can already be seen that adjustment with the invention is very simple since the height of the support 26 can be deduced merely by adding to the height Z both the radius of curvature R of the arc 22 and the height of the support 26 relative to the anchor point of the arc 22 between the pads 23 and 24, which height is fixed by construction, and making allowance for the difference between the insertion distance T and the radius R (which difference is also fixed).

The support 26 carries a plate 29 capable of moving in translation in the y direction under the action of a control button 30. In practice, the control button 30 may likewise be replaced by a motor-driven system. The action taken depends on the Y coordinate of the tumor: the displacement y is equal to Y after making allowance for the offset between the frames of reference in which they are measured. This offset can be made fixed by construction such that knowledge Y leads directly to the value of the displacement y, after making allowance for a constant offset. The plate 29 includes a further control 31 for displacing the shaft 21 in a slot 32. Here again, displacement in the x direction is simple, and is determined by construction such that $x = X \pm$ a constant offset. In addition, if it were necessary for the support 26 to be capable of taking an initial position that is arbitrary relative to the breast-carrying plate 3, it would then be necessary to be able to determine the effective starting heights of the support 26 and of the tumor 12 by means of an absolute scale integral with the post 2, e.g. the scale 33.

To make it possible to obtain any desired azimuth direction, at least over a circular arc 34 that extends preferably over 180°, the shaft 21 is mounted, for example, in ball bearings 35. The ball bearings may also be coupled to a brake (not shown) acting on the shaft 21 so as to lock the direction in which it points. The shaft 21 may be held in the ball bearings by means of collars, for example. The needle carrier 15 carries the needle 14 whose tip 13 is at a distance D from the position of the tumor. The distance D is a distance specific to the needle carrier. Consequently, once the needle is inserted, the tip 13 of the needle 14 moves from outside the breast to the location of the tumor 12.

The device of the invention then has the advantage of enabling the needle to be inserted from any direction. The choice of possible directions is limited only by the obstacles constituted by the pad and by the breast-carrying plate. These may be modified to satisfy a particular requirement. The equipment is then used as follows. By means of the buttons 28, 30, and 31 (or by means of their motor-driven equivalents under microprocessor control), the respective positions of the support 26, of the plate 30, and of the shaft 21 in the X direction are adjusted. It is recalled that x, y, and z displacements are known since they are equal to X, Y, and Z± respective constant offsets. It can also be observed that $X_a$, $Y_a$, and $Z_a$ are no longer relevant. Once the adjustments have been performed, the most appropriate insertion direction is selected as a function of reasons that are purely anatomic and that are independent of the mammograph. An elevation angle can be selected by sliding the arc 22 between the skids 23 and 24. Once the elevation angle has been selected, an azimuth direction can be selected by rotating the shaft 21 in the ball bearings 35. When these positions are reached, the control handle 25 and the rotary brake are actuated to lock the position of the assembly. Once this positioning has been completed, the needle is inserted.

The accompanying figures are diagrammatic, and other devices may be provided, in particular the arc 22 may be provided with a counterweight situated at the opposite end of the arc relative to the end carrying the needle carrier 15. This makes it possible for the arc to move in equilibrium between the skids 23 and 24.

FIG. 3 shows an embodiment in which the device of the invention can be used to obtain a vertical angle of incidence. In this case the shaft 21 includes a crank 36 to define an offset shaft 37. The skids 23 and 24 are fixed to the offset shaft 37. The offset shaft 37 is offset in the plane of rotation of the arc 22 between its skids.

As mentioned above, it is possible to choose to take a sample from or to fix the hook at a location that is not exactly the location of the tumor 12, but is slightly to one side. For example, it may be decided to perform an offset $\delta X$, $\delta Y$, or $\delta Z$, or even a combination of all three of these coordinates, and thereafter the surgeon will need to take account of this offset when making an incision. Adjusting the apparatus under such circumstances is very easy since it is merely necessary to define a fictitious isocenter situated at the offset $\delta$ from the exact location. The needle carrier is then adjusted on the fictitious isocenter.

FIG. 4 shows a simplified embodiment that can be used for implementing the invention. The structure with an arc 22 has been replaced by a crank-handle structure with the shaft 21 lying on the axis of the crank-handle. The handle has a crank 38 and a handle proper 39 to which the needle carrier 15 is fitted. This embodiment is intended for use, above all, with actions taken in a horizontal plane, in which case the crank 38 is at right angles both to the shaft 21 and to the handle proper 39.

We claim:

1. A mammograph comprising:
 means for holding a breast of a patient between an X-ray tube and a device for taking X-ray exposures;
 means for taking stereographic exposures of the breast;
 biopsy or surgical guidance means for acting on the breast at a determined location;
 said biopsy or surgical guidance means including a needle carrier which is displaceable relative to the breast;
 said needle carrier including a needle whose tip is displaceable along a selected length between a retracted position and an inserted position; and
 stereotaxic means associated with the above three means to calculate the position of a determined location at which action is to be taken;
 wherein the mammograph includes:
 pointing means for enabling the needle carrier to be pointable towards an isocenter situated at the determined location;
 said pointing means including a circular arc itself carried by a rotary shaft to provide two degrees of freedom in pointing the needle wherein the circular arc has a center of curvature which lies on the axis of the shaft carrying the circular arc.

2. A mammograph according to claim 1, wherein the stereotaxic means includes means for determining a starting position of the needle carrier, and means for causing insertion of the needle from the retracted position to the inserted position.

3. A mammograph according to claim 2, wherein the needle carrier pointing means comprise a crank handle having a substantially vertical axis passing through the determined location where action is to be taken.

4. A mammograph according to claim 1, wherein the stereotaxic means includes means for calculating the determined location at which intervention is to be performed and for deducing therefrom a direction in two planes in which the needle carrier is to be pointed.

5. A mammograph according to claim 1, wherein a needle insertion axis of the needle carrier and an axis of the rotary shaft carrying the needle carrier are situated in the same plane.

6. The mammograph according to claim 1, wherein the center of curvature of the circular arc coincides with the tip of the needle in its inserted position.

7. A mammograph comprising:
a carrying plate and pad for compressing and holding a breast of a patient in a fixed position;
stereography means for performing stereographic examination of the breast;
stereotaxic measurement means for calculating in three dimensions a determined location within the breast where action is to be taken;
a needle carrier displaceable in at least two directions;
the needle carrier being fixed on a rotary shaft by means of a circular arc, whereby the circular arc has a center of curvature which lies on an axis of the rotary shaft for pointing the needle carrier towards an isocenter situated at the determined location; and
a needle on the needle carrier extendable from a retracted position to the determined location.

8. The mammograph according to claim 7, wherein the rotary shaft is carried on a table displaceable in three directions.

9. The mammograph according to claim 8, further comprising motor-driven means on the table and controlled by a micro-processor for moving the rotary shaft in response to the stereotaxic measurement.

10. The mammograph according to claim 7, wherein the circular arc is slidable relative to the rotary shaft for selecting an elevation angle, and the rotary shaft is rotatable for selecting an azimuth direction for inserting the needle into the breast.

11. The mammograph according to claim 7, wherein the circular arc includes a T-shaped section with two chamfered flange ends and a chamfered base end, and the needle carrier includes a carriage which extends around the circular arc, wheel means bearing against the chamfered ends for adjusting the carriage, and brake pads for locking the carriage against the T-shaped section.

12. The mammograph according to claim 7, wherein the rotary shaft comprises a crank handle which includes a substantially vertical shaft having an axis passing through the determined location, and the crank handle includes an offset shaft, and the circular arc is fixed to the offset shaft.

13. The mammograph according to claim 7, wherein the axis of the needle and the axis of the rotary shaft are situated in a common plane.

14. The mammograph according to claim 7, wherein the center of curvature of the circular arc coincides with an end of the needle in its extended position.

15. A mammograph comprising:
means for compressing and holding a breast of a patient in a fixed position;
stereographic X-ray means for examining the breast;
stereotaxic measurement means for calculating a determined location at which action is to be taken on the breast;
a rotary shaft having an axis;
a circular arc on the rotary shaft, whereby the circular arc has a center of curvature which lies on the axis of the rotary shaft;
a needle carrier pointable along the circular arc towards an isocenter situated at the determined location; and
a needle on the needle carrier extendable from a retracted position to the determined location.

16. The mammograph according to claim 15, wherein the rotary shaft is displaceable in three directions.

17. The mammograph according to claim 15, further comprising motor-driven means controlled by a microprocessor for moving the rotary shaft above the determined location in response to the stereotaxic measurement means.

18. The mammograph according to claim 15, wherein the stereotaxic measurement means includes means for calculating in three dimensions the determined location at which action is to be taken on the breast and for deducing therefrom a direction in two planes in which the needle carrier is to be pointed.

19. The mammograph according to claim 15, wherein the rotary shaft comprises a crank handle which includes a substantially vertical portion having an axis passing through the determined location, and includes an offset position connected to the circular arc, whereby the needle carrier is pointable at a vertical angle toward the determined location.

20. The mammograph according to claim 15, wherein the stereographic measurement means include means for determining a starting position of the needle carrier, and means for causing insertion of the needle from the starting position to the determined location.

21. The mammograph according to claim 15, wherein the needle is insertable on an axis which is situated in a common plane as the axis of the rotary shaft.

22. The mammograph according to claim 15, wherein the center of curvature of the circular arc coincides with an end of the needle in its extended position.

* * * * *